(12) United States Patent
Nakamura

(10) Patent No.: US 10,478,268 B2
(45) Date of Patent: Nov. 19, 2019

(54) ELECTRIC MOTOR AND DENTAL DEVICE

(71) Applicant: NAKANISHI INC., Tochigi (JP)

(72) Inventor: Akito Nakamura, Tochigi (JP)

(73) Assignee: NAKANISHI INC., Tochigi (JP)

( * ) Notice: Subject to any disclaimer, the term of this patent is extended or adjusted under 35 U.S.C. 154(b) by 173 days.

(21) Appl. No.: 15/329,724

(22) PCT Filed: Jul. 30, 2015

(86) PCT No.: PCT/JP2015/003852
§ 371 (c)(1),
(2) Date: Jan. 27, 2017

(87) PCT Pub. No.: WO2016/017179
PCT Pub. Date: Feb. 4, 2016

(65) Prior Publication Data
US 2017/0215990 A1  Aug. 3, 2017

(30) Foreign Application Priority Data
Jul. 31, 2014 (JP) ................... 2014-156110

(51) Int. Cl.
*H02K 3/47* (2006.01)
*H02K 29/03* (2006.01)
(Continued)

(52) U.S. Cl.
CPC ............. *A61C 1/06* (2013.01); *A61C 1/003* (2013.01); *A61C 1/0061* (2013.01); *A61C 1/088* (2013.01);
(Continued)

(58) Field of Classification Search
CPC .......... A61C 1/06; A61C 1/088; A61C 1/003; A61C 1/0061; A61C 1/12; H02K 29/03; H02K 2213/12; H02K 3/47
(Continued)

(56) References Cited

U.S. PATENT DOCUMENTS

| 4,837,921 A * | 6/1989 | Tassinario ............... H02K 1/12 264/272.2 |
| 5,323,075 A * | 6/1994 | Denk ..................... H02K 29/08 310/216.102 |

(Continued)

FOREIGN PATENT DOCUMENTS

| DE | 102006015037 A1 | 10/2007 |
| EP | 0788779 A2 | 8/1997 |

(Continued)

OTHER PUBLICATIONS

English translation of International Search Report for PCT/JP2015/003852 dated Oct. 27, 2015.
(Continued)

*Primary Examiner* — John K Kim
(74) *Attorney, Agent, or Firm* — Pearne & Gordon LLP

(57) ABSTRACT

An electric motor that enables to promote a further downsizing and performance enhancement, and a dental device that includes the electric motor. A brushless slotless electric motor 10 includes: a stator 3 that includes a stator core 301 and a plurality of coils 31 to 33 disposed inside of the stator core 301; a rotor 2 that includes a shaft 21, the rotor 2 being rotated around the shaft 21 with respect to the stator 3; and a medium pathway 40 through which a medium passes, the medium being supplied for actualizing a function of a dental handpiece 9A to which the electric motor 10 is applied. The plurality of coils 31 to 33 are adjacent to each other in a rotation direction of the rotor 2 so as not to lap mutually. The medium pathway 40 is disposed between the adjacent coils 31 to 33.

16 Claims, 11 Drawing Sheets

(51) Int. Cl.
*A61C 1/06* (2006.01)
*A61C 1/12* (2006.01)
*A61C 1/00* (2006.01)
*A61C 1/08* (2006.01)

(52) U.S. Cl.
CPC .............. *A61C 1/12* (2013.01); *H02K 29/03* (2013.01); *H02K 3/47* (2013.01); *H02K 2213/12* (2013.01)

(58) Field of Classification Search
USPC .......................................................... 310/50
See application file for complete search history.

(56) References Cited

U.S. PATENT DOCUMENTS

| | | | |
|---|---|---|---|
| 5,460,503 A | 10/1995 | Kitajima et al. | |
| 7,928,619 B2* | 4/2011 | Watanabe | H02K 1/12 310/179 |
| 8,063,547 B2* | 11/2011 | Makino | H02K 15/0031 310/216.115 |
| 9,537,376 B2* | 1/2017 | Duesing | H02K 5/08 |
| 2008/0305455 A1 | 12/2008 | Guscott | |
| 2009/0160270 A1 | 6/2009 | Bischof et al. | |
| 2009/0160271 A1* | 6/2009 | Bischof | A61C 1/185 310/52 |
| 2009/0243424 A1* | 10/2009 | Watanabe | H02K 1/12 310/216.109 |
| 2010/0019588 A1* | 1/2010 | Makino | H02K 15/0031 310/52 |
| 2010/0301688 A1 | 12/2010 | Schulz et al. | |
| 2013/0313933 A1* | 11/2013 | Kawasaki | H02K 1/276 310/156.11 |
| 2013/0342050 A1* | 12/2013 | Duesing | H02K 5/08 310/59 |
| 2014/0125180 A1* | 5/2014 | Thaler | H02K 3/24 310/156.01 |
| 2015/0229175 A1* | 8/2015 | Miyashita | H02K 3/30 310/43 |
| 2017/0215990 A1* | 8/2017 | Nakamura | A61C 1/06 |

FOREIGN PATENT DOCUMENTS

| | | |
|---|---|---|
| GB | 2385210 A | 8/2003 |
| JP | 2001086721 A | 3/2001 |
| JP | 2002-233126 A | 8/2002 |
| JP | 3750790 B2 | 12/2005 |
| JP | 2009-153374 A | 7/2009 |
| JP | 2012-521185 A | 9/2012 |
| JP | 2015-123143 A | 7/2015 |
| KR | 1020140088268 A | 7/2014 |
| WO | 0215229 A1 | 2/2002 |

OTHER PUBLICATIONS

Extended European Search Report for Application No. EP15827154, dated Mar. 2, 2018.

Office Action for European Application No. 15827154.4, dated Nov. 20, 2018.

Office action for European application No. 15827154.4 dated Jun. 18, 2019.

\* cited by examiner

ELECTRIC MOTOR AND DENTAL DEVICE

TECHNICAL FIELD

The present invention relates to a small brushless slotless motor, and for example, relates to a motor that is applied to a dental handpiece, and a dental device.

BACKGROUND ART

As an electric motor that drives a dental handpiece including a tool, a brushless slotless motor is used, for the sake of the suppression of rotation unevenness and vibration (for example, Patent Literature 1 and Patent Literature 2).

A plurality of coils provided on a bobbin are disposed at the inner circumference of a cylindrical stator core of the motor.

The motor that is applied to the dental handpiece is provided with pathways through which water and air pass. The water and air introduced into the handpiece through those pathways are supplied from the position of the tool of the handpiece into the mouth cavity. In the case where the handpiece has a lighting function, the motor is provided also with a pathway through which an electric wire for lighting passes.

The dental motor requires a downsizing that allows an operator to easily perform operation in hand, in addition to a sufficient torque output (performance) for stably performing the cutting and polishing with the tool. In order to achieve a small high-performance motor, in the internal space of the case, it is desirable to reduce a region that does not contribute to the performance as much as possible, and secure a large region that can be effectively used on the magnetic circuit.

Here, as the kind of a coil (winding wire) of the slotless motor, there are a lap winding in which coils are disposed so as to lap over each other, and a non-lap winding in which coils are disposed so as not to lap over each other.

As an example of the lap winding, there is Patent Literature 1. In the lap winding, as shown in FIG. 11A, on the inside of an opening 100 of each of coils 101 to 103, a coil side 10s (coil straight) of another coil is disposed. Then, the coils 101 to 103 are lapped over each other, at coil ends 10e.

FIG. 11B schematically shows a cross-section of a portion where the coil 101 and the coil 102 lap at the coil ends 10e. Hatched lines are given on a cross-section of the coil 102. The coil side 10s of the coil 102 is disposed on the inside of the opening 100 of the coil 101, while the coil end 10e of the coil 102 is lapped over the coil end 10e of the coil 101. In this way, as the whole of the coils 101 to 103 lapped at the coil ends 10e, the coil ends 10e are formed so as to be thicker than the coil side 10s, and protrude in radial directions relative to the coil side 10s.

In the case of the lap winding, the pipes as the pathways for water and air and the electric wire for lighting are weaved into the interior of the coil ends 10e, and the coil is shaped. Thereby, it is possible to integrate the pipes and the electric wire with the coil. In such a complex lap winding structure, the coil tightly contacts with the pipes and the electric wire at the coil ends 10e. Therefore, an excessive stress is likely to be given on the coil, and the production cost is high. Further, because of the complex structure, the design change such as the increase in the space factor that is the proportion of conductors to the cross-section area of the coil is not easy.

Furthermore, in the lap winding, as shown in FIG. 11B, the coil ends 10e protrude in radial directions relative to the coil side 10s, and a stator core 105 whose diameter is set so as to be equivalent to the outer diameter of the coil side 10s cannot be provided to the coil ends 10e. Therefore, the length of the motor that can be effectively used is shortened by the length of the coil ends 10e, with the restriction of the length of the motor due to the requirement of downsizing. The whole circumference of the coil ends 10e is an ineffective region that does not contribute to the performance of the motor. Although the coil ends 10e protrude in radially outward directions in the above case, in the case where the coil ends 10e protrude in radially inward directions, a rotor 106 whose diameter is set so as to be equivalent to the inner diameter of the coil side 10s cannot be provided to the coil ends 10e, and therefore, the effective length of the motor is shortened, similarly.

On the other hand, as an example of the non-lap winding, there is Patent Literature 2.

In the case of the non-lap winding, since the coils do not lap over each other, the coil can be shaped into a simple shape. Therefore, the production cost is reduced. Further, the stator core can be provided over the whole length of the coil in the axial direction.

In the Patent Literature 2, in which the non-lap winding is employed, the pathways for water, air and the lighting electric wire are disposed at the outside of the stator core.

CITATION LIST

Patent Literature

Patent Literature 1: European Patent Application Publication No. 0788779
Patent Literature 2: Japanese Patent No. 3750790

SUMMARY OF INVENTION

Technical Problem

In the configuration of Patent Literature 2, the outside of the stator core, at which the pathways for water, air and lighting electric wire are disposed, is an ineffective region on the magnetic circuit, over the whole circumference and the whole length of the motor. That is, the outer diameter of the motor that can be effectively used becomes small by the length of the pathways, with the restriction of the diameter of the motor due to the requirement of downsizing.

The above pathways each need to be provided somewhere in a motor case, for playing functions of the supply of water and air and the supply of electric power to a light source, but it can be said that the intervals among the pathways are useless regions that occupy space in the motor case but do not function.

As described above, in both the case of the lap winding and the case of the non-lap winding, an ineffective region is generated on the magnetic circuit. The ineffective region means a region that does not contribute to the output of the motor regardless of whether a structure exists there.

The present invention has been made in view of the technical problem described above, and has an object to provide an electric motor that enables to promote a further downsizing and performance enhancement, and a dental device that includes the electric motor.

Solution to Problem

A brushless slotless electric motor according to the present invention includes: a stator that includes a stator core and a plurality of coils, the plurality of coils being disposed at an inside of the stator core; a rotor that includes a shaft, the rotor being rotated around the shaft with respect to the stator; and a medium pathway through which a medium passes, the medium being used for actualizing a function of an application object of the electric motor.

Then, the present invention is characterized in that the plurality of coils are adjacent to each other in a rotation direction of the rotor so as not to lap mutually, and the medium pathway is disposed between the adjacent coils.

Here, examples of the "medium" in the present invention include a fluid such as water and air that is used for actualizing functions such as the cleaning and cooling of the application object, and an electric wire or light that is used for actualizing functions such as lighting and sensing. The "medium pathway" is a pathway (space) that is necessary for the passing of such a medium. For example, if the medium is a fluid, the "medium pathway" corresponds to a space occupied by a channel (a pipe or the like) through which the fluid passes, and if the medium is an electric wire or light, it corresponds to a space occupied by the electric wire or a light transmission member.

In the specification, the rotation direction of the rotor is defined as the "circumferential direction".

Further, in the specification, unless otherwise mentioned, the "axial direction" of a certain matter is a direction identical to the axial direction of a shaft included in the rotor, or a direction parallel to the axial direction of the shaft.

In the specification, the "radial direction" of a certain matter means an arbitrary direction orthogonal to the "axial direction".

Furthermore, in the specification, unless otherwise mentioned, the "outer circumference" of a certain matter means an outside site of the matter along the rotation direction of the rotor, and the periphery of the site. The outside site described here is referred to as the "outer circumference portion". The radially outer side relative to the "outer circumference portion" is referred to as the "outside of the matter".

Then, in the specification, unless otherwise mentioned, the "inner circumference" of a certain matter means an inside site of the matter along the rotation direction of the rotor, and the inside relative to the site. The inside site described here is referred to as the "inner circumference portion". The radially inner side relative to the "inner circumference portion" is referred to as the "inside of the matter".

In other words, the electric motor in the present invention for solving the above problem has the following configuration. Here, the electric motor supplies drive force to a member (for example, a bar for cutting) included in a drive target (for example, a dental handpiece). The electric motor includes a stator, a rotor that is rotated with respect to the stator, and at least one pathway (a space occupied by a pipe through which water or air passes or an electric wire for supplying electric power) that is provided in the stator. The pathway provides, to the drive target, an ability to achieve a function (cooling, cleaning, lighting or the like) other than the above-described motion (rotation, cutting or the like) of the member. The stator includes a cylindrical stator core, and a plurality of coils that are disposed at the inside of the stator core. Each of the plurality of coils is disposed at the inside of the stator core along the rotation direction of the rotor. Here, when one of the plurality of coils is specified as a specified coil, the specified coil is disposed so as not to lap over an adjacent coil, and the above-described pathway is formed at a border gap between the two adjacent coils.

The present invention employs the non-lap winding in which the coils do not lap mutually, and therefore, unlike the case of the lap winding, a magnetic ineffective region is not generated at the coil end.

Furthermore, according to the present invention, it is possible to put the medium pathway in the gap between the adjacent coils, without giving an excessive stress on the coils. Thereby, the medium pathway is embedded in the interior of a main element (the rotor and the stator) that performs the drive of the motor, and therefore, a space for disposing the medium pathway is not necessary, at the outside of the main element.

Therefore, as described in detail in the section of Description of Embodiments, it is possible to use the ineffective region that has been used for the medium pathway at the outside of the main element of the motor, for bringing out the motor output.

Thereby, it is possible to achieve the downsizing by reducing the diameter of a motor case while securing the outer diameter of the main element of the motor that is appropriate to a required output, and it is possible to achieve the performance enhancement by securing a larger outer diameter as the outer diameter of the main element while maintaining a small diameter as the diameter of the motor case.

In other words, it is possible to enhance the performance per size of the motor case.

In the electric motor according to the present invention, it is preferable that the medium pathway be a space occupied by a pipe through which a fluid as the medium passes, or a space occupied by an electric wire as the medium, and a thickness of the pipe or the electric wire be set to smaller than or equal to a thickness of the coil.

Thereby, the pipe or the electric wire does not protrude to the outside of the coils, and therefore, there is no trouble of processing a groove as an undercut for the pipe or the electric wire, on the stator core. Further, it is possible to avoid such a groove from exerting influence on the magnetic characteristic.

It is preferable that the electric motor in the present invention include a holder member that holds the plurality of coils, in which the holder member includes: a cylinder portion that has the plurality of coils disposed on an outer circumference thereof; and a flange that projects from the cylinder portion in a radially outward direction, and the medium pathway penetrates the flange.

A hole or a cutout through which the medium pathway passes is formed on the flange of the holder member.

In the present invention, in which the medium pathway is disposed between the adjacent coils, it is only necessary to form the flange that the medium pathway penetrates, on the holder member that holds the coils, for supporting the pipe or electric wire configuring the medium pathway.

The flange can be formed at one end or both ends of the holder member.

The electric motor in the present invention can be configured such that the stator includes three coils, and the rotor includes four poles.

Thereby, it is possible to efficiently obtain the output torque.

The electric motor in the present invention is suitable for driving a dental handpiece that is an application object. In that case, the electric motor can include, as the medium pathway, a pathway through which water to be supplied into the dental handpiece passes, and a pathway through which air to be supplied into the dental handpiece passes. In the case where the handpiece has a lighting function, the electric motor in the present invention preferably should further include, as the medium pathway, a pathway through which an electric wire for lighting passes.

A dental device in the present invention includes: the above-described electric motor; a dental handpiece that is driven by the electric motor; and a controller that performs drive control of the electric motor.

In the dental device in the present invention, it is preferable that the electric motor be connected with the controller through a hose, and the medium pathway be positioned on an extended line or approximately on an extended line of a pathway that is formed in the hose.

In that case, it is possible to configure a linear pathway from the pathway in the hose to the medium pathway in the motor, and therefore, it is possible to inhibit foreign substances from accumulating in the pathway, unlike the case where a curved spot is formed on the pathway. Thereby, it is possible to stably supply the medium such as water and air.

Advantageous Effects of Invention

According to the present invention, it is possible to provide an electric motor that enables to promote a further downsizing and performance enhancement, and a dental device that includes the electric motor.

BRIEF DESCRIPTION OF DRAWINGS

FIGS. 2A to 2C show a dental motor according to the embodiment of the present invention, in which FIG. 2A is a diagram viewed from the front side, FIG. 2B is a lateral view and FIG. 2C is a diagram viewed from the rear side.

FIG. 11 shows a conventional example of a lap winding, in which

DESCRIPTION OF EMBODIMENTS

Figure 1:
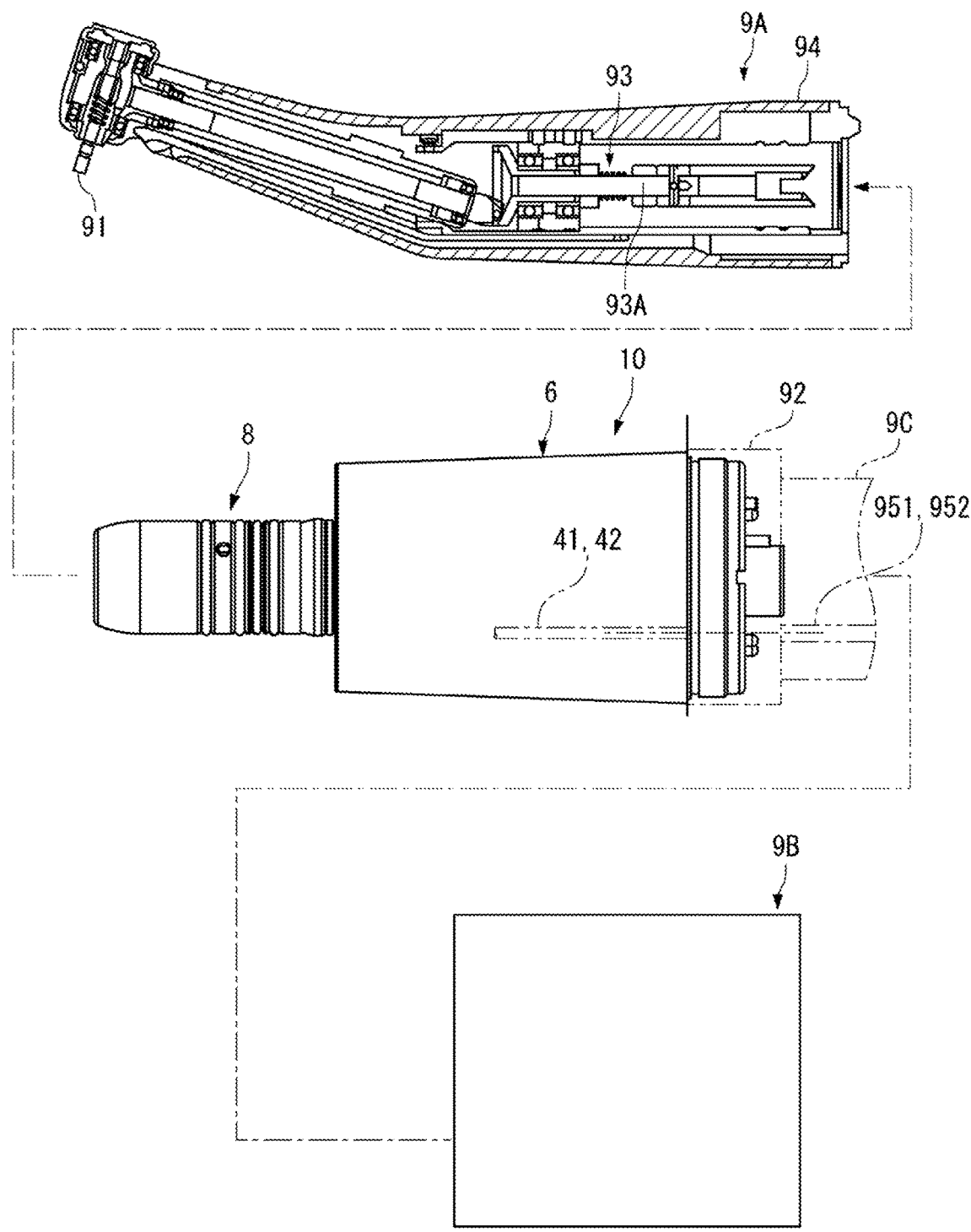
FIG. 1 is a diagram showing a dental device according to an embodiment of the present invention.

Hereinafter, an embodiment of the present invention will be described with reference to the accompanying drawings.
[Schematic Configuration of Dental Device]
As shown in FIG. 1, a dental device according to the embodiment includes a dental handpiece 9A, a motor 10 that drives the handpiece 9A, and a controller 9B that performs the drive control of the motor 10, and the like. The dental device transmits the torque obtained by the motor 10, to a tool 91 positioned at a front end of the handpiece 9A, and cuts teeth with the tool 91 that is driven so as to be rotated.

Further, the dental device in the embodiment lights a cut site in the mouth cavity by the light emitted from the front end of the handpiece 9A, and cleans the cut site by the water and air discharged from the front end similarly. It is preferable that the discharge pressures of the water and air and the light intensity be controlled by the controller 9B.
[Schematic Configuration of Dental Motor]
FIG. 1 and FIGS. 2A to 2C show the external appearance of the motor 10 in the embodiment.

The handpiece 9A is attached to one end side of the motor 10. A hose 9C is provided on the other end side of the motor 10, through a connector 92. The motor 10 and the handpiece 9A are connected with the controller 9B through the hose 9C.

Figure 3:
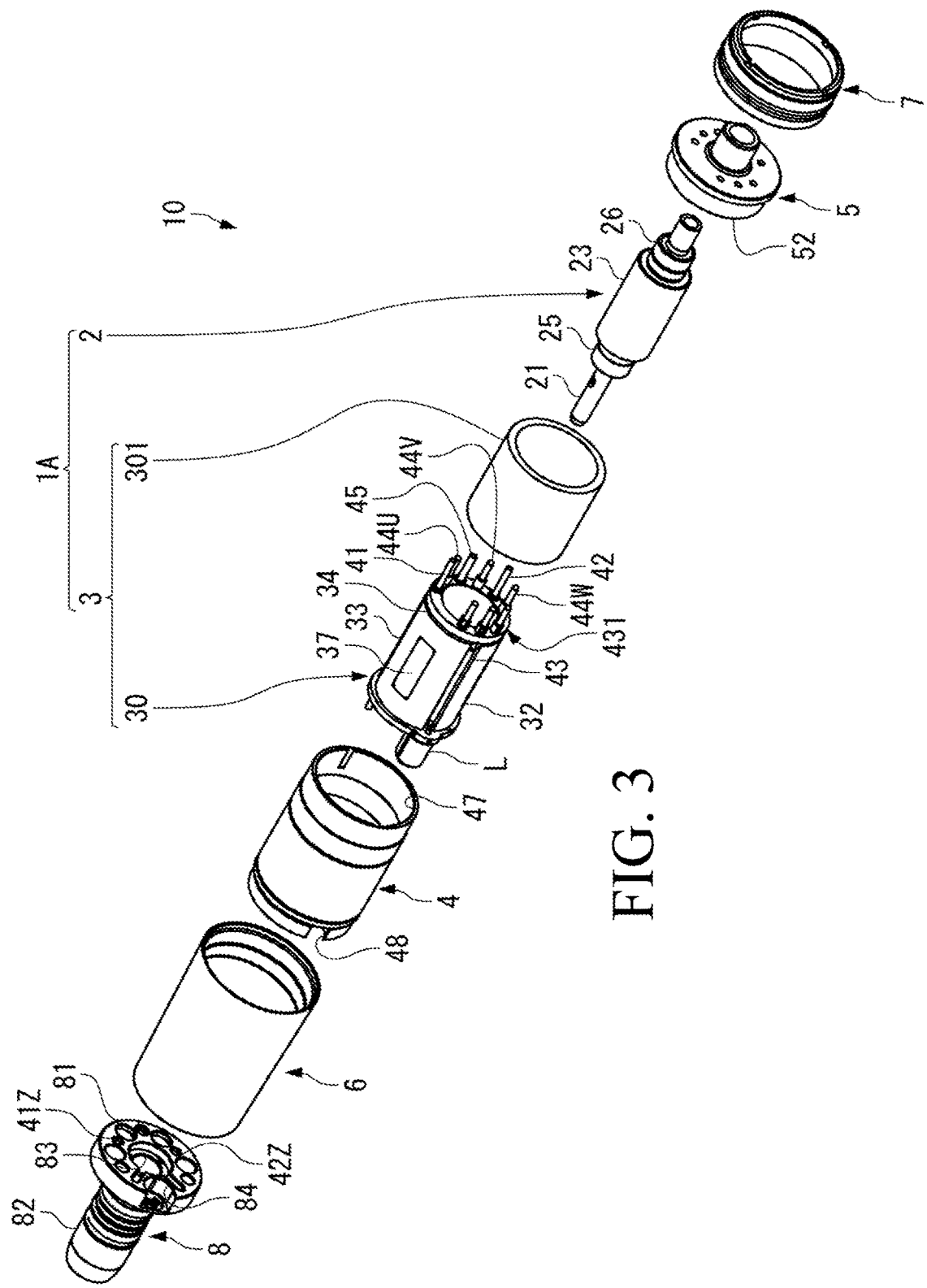
FIG. 3 is an exploded perspective view of the motor shown in FIGS. 2A to 2C.

In the specification, in the motor 10, the side to which the handpiece 9A is attached is defined as "front", and the opposite side (the connector 92 side) is defined as "rear".
[Constituent Element of Motor]
As shown in FIG. 3, the motor 10, which is a brushless slotless motor, includes a rotor 2 and a stator 3 of a main element 1A that performs drive, a holder case 4 for storing and holding them, a rear holder 5, a motor case 6, a ring screw 7, an insert cylinder 8 to which the handpiece 9A is attached in a detachable manner.

Figure 5:
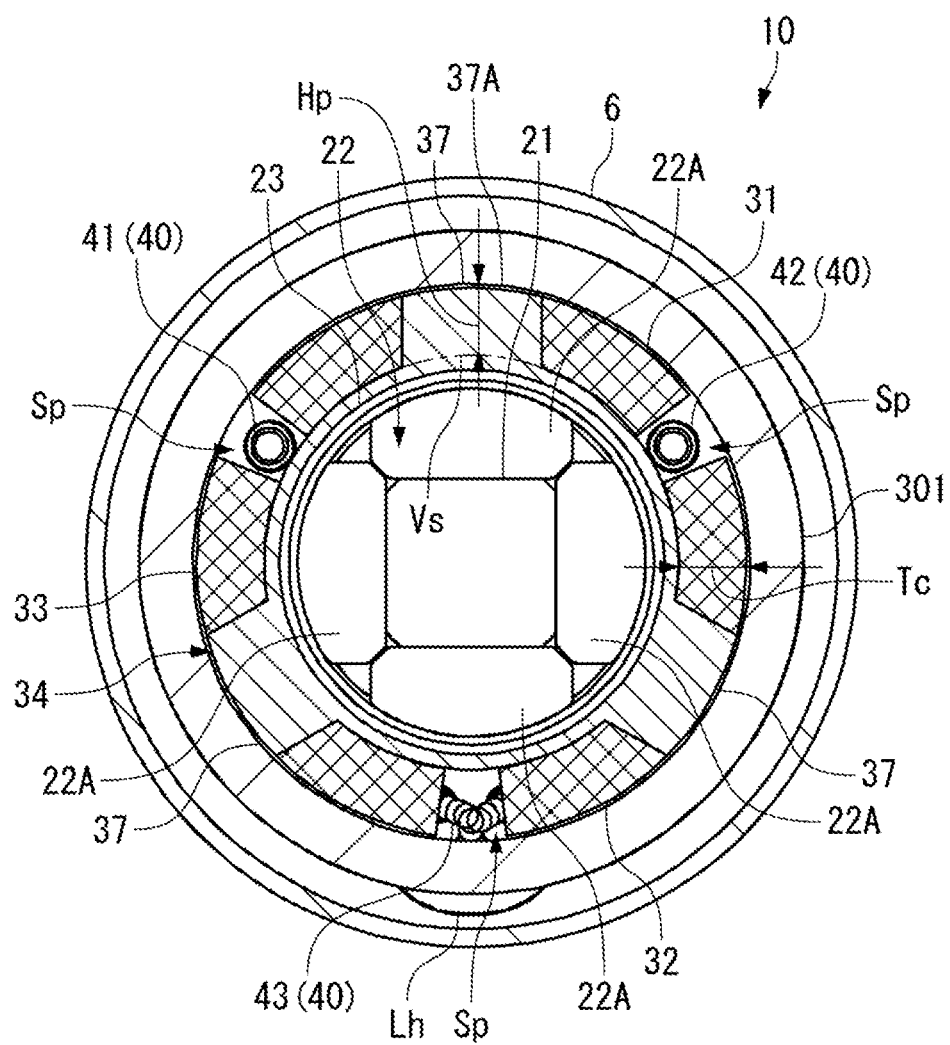
FIG. 5 is a V-V line arrow view of FIG. 2B (transverse cross-sectional view).
Figure 6:
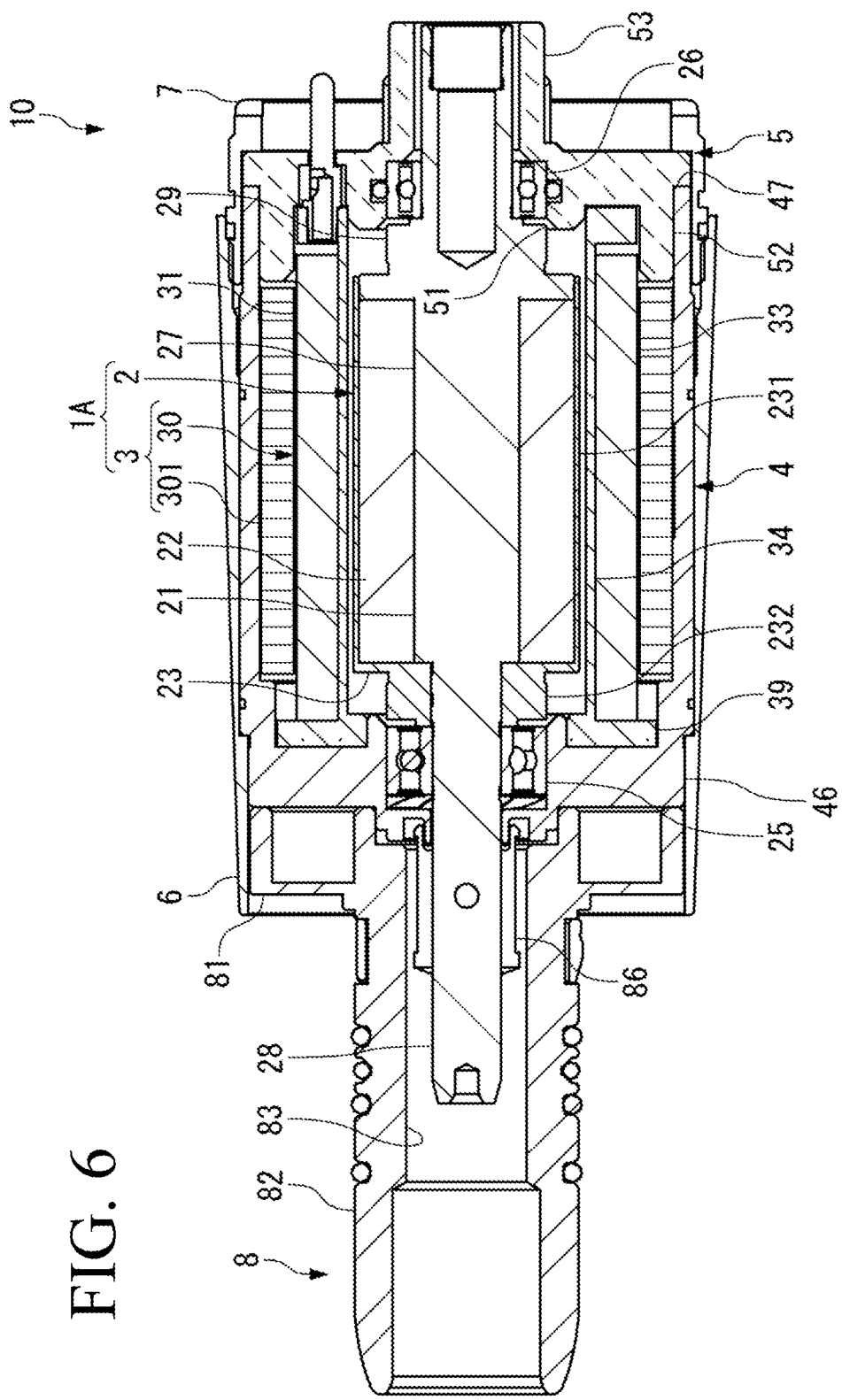
FIG. 6 is a VI-VI line arrow view of FIG. 2B (longitudinal cross-sectional view).

Hereinafter, these constituents will be described in order.
[Rotor]
As shown in FIG. 3, FIG. 5 and FIG. 6, the rotor 2 includes a shaft 21, a magnet 22 fixed to the shaft 21, which is a permanent magnet, and a cover holder 23 that covers the outer circumference portion of the magnet 22.

The magnet 22, which includes four poles, is constituted by four divided segments 22A, as shown in FIG. 5.

Instead of these segmented magnets, an integrated magnet that is magnetized for four poles may be used, and both of radial anisotropy and polar anisotropy can be employed as the magnetic field orientation.

As shown in FIG. 6, the shaft 21 includes a central portion 27 at which the magnet 22 is provided, a front end portion 28 that is positioned at the front side of the central portion 27, and a rear end portion 29 that is positioned at the rear side of the central portion 27.

As shown in FIG. 3 and FIG. 6, a front bearing 25 is provided on the side of the front end portion 28 of the shaft 21, and a rear bearing 26 is provided on the side of the rear end portion 29 of the shaft 21. Each of these bearings 25, 26 is a ball bearing that includes spherical rolling elements (balls) between an inner ring and an outer ring.

As shown in FIG. 6, the cover holder 23 includes a cover portion 231 that covers the outer circumference portion of the magnet 22, and a front end portion 232 on which the front end of the magnet 22 abuts.
[Stator]
Next, as shown in FIG. 3, the stator 3 includes a coil unit 30, and a cylindrical stator core 301 that is disposed on the outer circumference of the coil unit 30.

Figure 4:
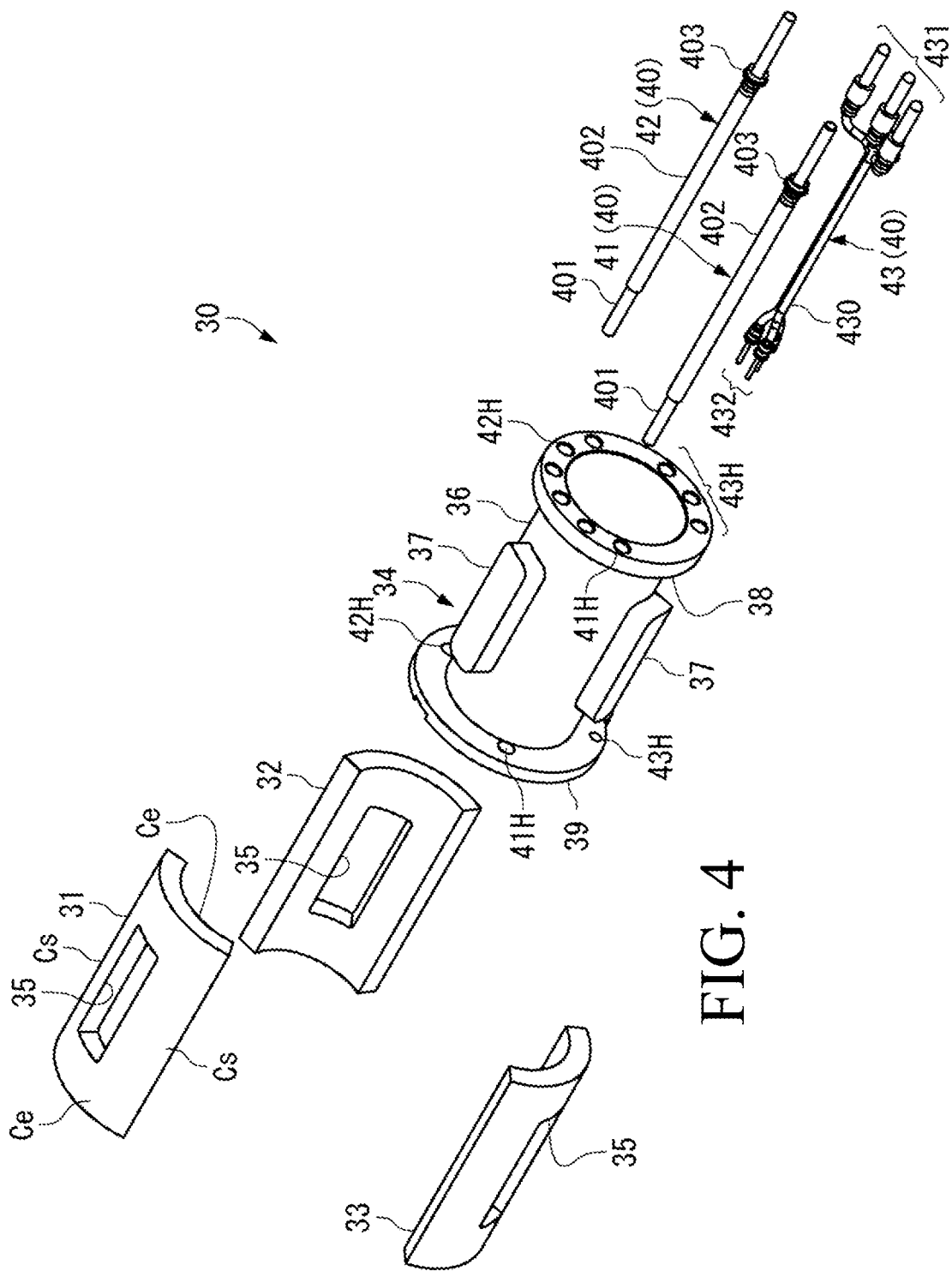
FIG. 4 is an exploded perspective view of a coil unit that is included in the motor shown in FIG. 2.

The stator core 301 is formed by laminating annular plates formed of magnetic metal.
(Coil Unit)
As shown in FIG. 4, the coil unit 30 includes three coils (winding wires) 31, 32, 33, a bobbin 34 (holder member) that holds the coils 31 to 33, a water injection pipe (first pipe) 41, a chip air pipe (second pipe) 42, and a lighting electric wire 43.

Figure 7:
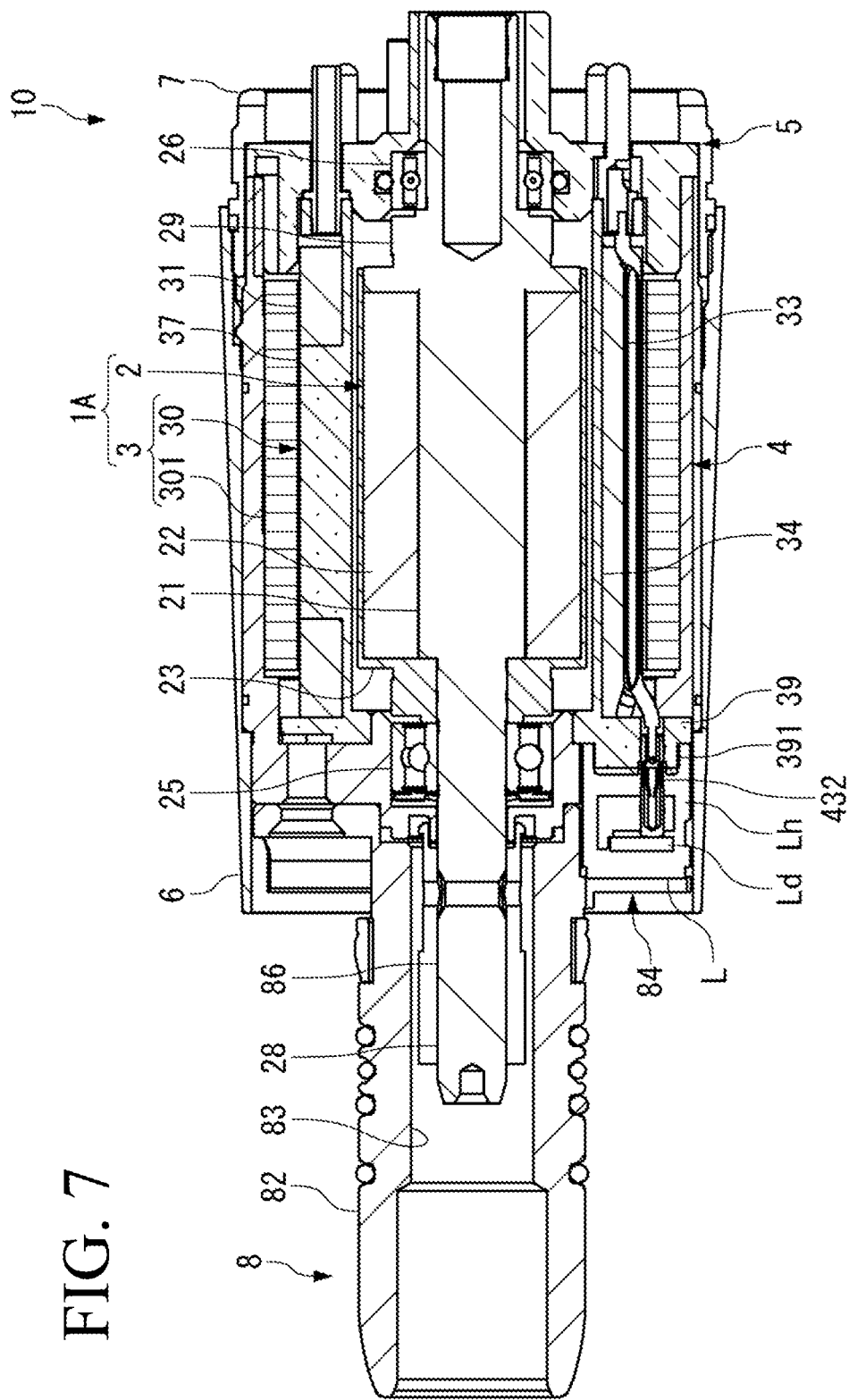
FIG. 7 is a VII-VII line arrow view of FIG. 2A (longitudinal cross-sectional view).

A light source L (FIG. 3) to which electric power is supplied through the lighting electric wire 43 is incorporated into the coil unit 30 (FIG. 3 and FIG. 7).

The light source L includes a light emitting device Ld such as a white LED (Light Emitting Diode), and a housing Lh that holds the light emitting device Ld. The light emitting device Ld can be constituted by a single or a plurality of LEDs.

(Coil)

As shown in FIG. 4, the coil 31 is wound so as to have a rectangular shape in planar view, using a coated conductive wire in which a good conductor such as copper is coated with resin, and is shaped into a shape that is curved along the outer circumference portion of the bobbin 34. The coil 31 has coil sides Cs and coil ends Ce. The coil sides Cs are linear sections that are disposed along the axial direction of the stator core 301. The coil ends Ce are sections that are positioned at both ends in the axial direction.

The other coils 32, 33 are formed similarly to the coil 31. These coils 31 to 33 are connected so that an armature coil is formed.

The sizes of the coils 31 to 33 in the radial direction of the rotor 2 when the coils 31 to 33 are disposed at the periphery of the rotor 2 are defined as the thicknesses of the coils 31 to 33. Taking the coil 32 as an example, the thickness Tc of the coil 32 is shown in FIG. 5. Each of the coils 31 to 33 is formed so as to have the same thickness Tc.

Each of the coils 31 to 33 is formed so as to have an even thickness from one end to the other end in the rotation direction of the rotor 2. However, a slight unevenness of the thickness due to tolerance and the like is permitted.

For the coils 31 to 33, a round wire having a circular cross-section, a flat wire having a rectangular cross-section, or the like can be used.

The coils 31 to 33 are not limited to a rectangular shape in planar view, and may have an arbitrary shape such as a track shape, an ellipse and an oval.

The embodiment employs a non-lap winding as the disposition of the coils 31 to 33. The coils 31 to 33 each extend on independent regions that are less than 120° with respect to the shaft center of the shaft 21, and are disposed so as to be adjacent in the rotation direction of the rotor 2 without lapping over each other. In the non-lap winding, it is possible to shorten the length of one winding of the coil, compared to a lap winding in which the coil extends over a region of 180°, and therefore, it is possible to reduce coil resistance in the case of the same winding number. The smaller resistance can contribute to the enhancement of the output of the motor.

For efficiently operating the motor in the non-lap winding, the four-pole rotor 2 can be suitably employed for the three coils 31 to 33, as in the case of the embodiment. For the same reason, 3n coils and a 4n-pole rotor can be suitably employed (n is a natural number).

In addition, the combination of 3 nm coils and a 2n-pole rotor can be employed (n and m are natural numbers). For example, the combination of 3 coils and a 2-pole rotor, the combination of 6 coils and a 2-pole rotor, and the like are applicable.

Here, the central angle of the region where the coil extends is not limited to the above angle, and can be set to an appropriate angle depending on the number of coils.

A gap Sp (FIG. 5) having a predetermined size is set between the adjacent coils of the coils 31 to 33. In the embodiment, there are three gaps Sp, and in these gaps Sp, the water injection pipe 41, the chip air pipe 42 and lighting electric wire 43 are disposed respectively.

(Bobbin)

As shown in FIG. 4, the bobbin 34, which is formed of an insulating resin, integrally includes a cylinder portion 36 that has a cylindrical shape and that is disposed coaxially with the shaft 21, three convex portions 37 that are provided so as to protrude from the outer circumference portion of the cylinder portion 36, a rear flange 38 that is positioned at a rear end of the cylinder portion 36, and a front flange 39 that is positioned at a front end of the cylinder portion 36.

The convex portion 37 is formed so as to have a height Hp (FIG. 5) nearly equal to the thickness Tc of the coils 31 to 33, and is formed in a shape corresponding to an opening 35 at the inside of each of the coils 31 to 33, that is, here, in an ellipse shape in planar view that is long in the axial direction of the shaft 21. The convex portions 37 are disposed at regular intervals in the circumferential direction of the bobbin (FIG. 5), and the coils 31 to 33 are fitted to the convex portions 37.

The height Hp of the convex portion 37 means the size of the convex portion 37 that is measured along the radial direction of the bobbin 34. More specifically, as shown in FIG. 5, the height Hp is the size that is measured from a virtual surface Vs (shown by a long dashed short dashed line) resulting from expanding the outer circumference surface of the cylinder portion 36 to the base end of the convex portion 37, to a top surface 37A of the convex portion 37 along the radial direction.

The convex portion 37 positioned in the opening 35 of each of the coils 31 to 33 has the function of the positioning and holding in the circumferential direction and axial direction of the coils 31 to 33. As long as the function can be fulfilled, the convex portion 37 may have any shape.

The rear flange 38 and the front flange 39 protrude from the cylinder portion 36 in the radially outward direction. On these flanges 38, 39, a plurality of through-holes passing in the thickness direction are formed. The rear flange 38 projects from the cylinder portion 36 by a size equivalent to the height of the convex portion 37, and is put in the inside of a fitting portion 52 of the rear holder 5 described later. The front flange 39 is larger than the rear flange 38 in the protruding size from the cylinder portion 36, and is put in the inside of the holder case 4.

On the front flange 39, a protrusion 391 (FIG. 7) that protrudes forward is formed. The protrusion 391 engages with the housing Lh of the light source L, and thereby, the light source L is provided in the bobbin 34.

(Pipes for Water and Air, Lighting Electric Wire)

As shown in FIG. 4, the water injection pipe 41, the chip air pipe 42 and the lighting electric wire 43 are disposed along the axial direction of the bobbin 34, in the range from the rear flange 38 to the front flange 39.

The water injection pipe 41 includes a metal pipe 401 that linearly extends along the axial direction, and a resin cover 402 that is attached to the outer circumference portion of the metal pipe 401. Both end portions of the metal pipe 401 are exposed from the resin cover 402.

The water injection pipe 41 passes through holes 41H that are formed on the rear flange 38 and the front flange 39 respectively. An engagement portion 403 formed on the resin cover 402 engages with a rim portion of the hole 41H of the rear flange 38, and thereby, the water injection pipe 41 is fixed to the bobbin 34.

The rear end side of the water injection pipe 41 is connected through the connector 92 with a tube 951 in the hose 9C (FIG. 1) through which water is pumped by a pump (a supply source of water). The front end side of the water injection pipe 41 is connected with a terminal end of a pathway provided in the handpiece 9A, through a pathway formed in the insert cylinder 8. Water is supplied from a discharge port provided at a leading end of the pathway, into the mouth cavity.

Here, in FIG. 1, the pipes 41, 42 are illustrated at the same position, and also, tubes 951, 952 are illustrated at the same position.

The chip air pipe 42 configured similarly to the water injection pipe 41 also passes through holes 42H that are formed on the rear flange 38 and the front flange 39 respectively, and is fixed to the bobbin 34.

The rear end side of the chip air pipe 42 is connected through the connector 92 with the tube 952 in the hose 9C (FIG. 1) through which air is introduced by an air compressor (a supply source of air). The front end side of the chip air pipe 42 is connected with a terminal end of a chip air pathway provided in the handpiece 9A, through a pathway formed in the insert cylinder 8. Air is supplied from an injection port provided at a leading end of the pathway, into the mouth cavity.

As shown in FIG. 1, it is preferable that the water injection pipe 41 be positioned on an extended line of the tube 951 in the hose 9C. Similarly, it is preferable that the chip air pipe 42 be positioned on an extended line of the tube 952 in the hose 9C.

Here, it is not necessary to be strictly on the extended line, and the positions of the pipes 41, 42 may slightly deviate from the positions of the corresponding tubes 951, 952 (it is allowed to be approximately on the extended line).

The lighting electric wire 43 includes a wiring portion 430 in which a plurality of conductive wires are stored in a resin sheath, and lighting terminals 431, 432 that are positioned at both ends of the wiring portion 430.

The lighting terminals 431 positioned at a rear end of the wiring portion 430 are inserted into holes 43H of the rear flange 38, and the lighting terminals 432 positioned at a front end of the wiring portion 430 are inserted into holes 43H of the front flange 39, so that the lighting electric wire 43 is fixed to the bobbin 34. The lighting terminal 431 is connected with the electric wire in the hose 9C, through the connector 92. The lighting terminal 432 is connected with the light source L (FIG. 7). The light emitted by the light source L is led to the front end of the handpiece 9A, through an optical fiber (unillustrated) that is a light transmission pathway.

The water injection pipe 41, the chip air pipe 42 and the lighting electric wire 43 are put in the gaps Sp that are formed among the coils 31 to 33 (FIG. 5). In the coils 31 to 33 shaped in a simple shape, it is possible to accurately manage the sizes, resulting in a high accuracy of the sizes and positions of the gaps Sp, which are residual portions of the outer circumference portion of the bobbin 34 when the coils 31 to 33 are disposed in the bobbin 34. Accordingly, the pipe 41 and the like do not interfere with the coils, and stress is not applied to the coils 31 to 33. It is possible to put the water injection pipe 41, the chip air pipe 42 and the lighting electric wire 43 between the adjacent coils 31 to 33, with no difficulty.

The incorporation of the water injection pipe 41, the chip air pipe 42 and the lighting electric wire 43 into the bobbin 34 can be performed after the coils 31 to 33 are incorporated into the bobbin 34, or before the coils 31 to 33 are incorporated into the bobbin 34.

In the case where the thickness (outer diameter) of each of the water injection pipe 41, the chip air pipe 42 and the lighting electric wire 43 is identical or nearly identical to the size in the circumferential direction of the gaps Sp among the coils 31 to 33, the water injection pipe 41, the chip air pipe 42 and the lighting electric wire 43 can be utilized for the positioning and holding of the coils 31 to 33. In that case, it is allowable to omit the formation of the convex portion 37 of the bobbin 34.

It is preferable that the thickness (outer diameter) of each of the water injection pipe 41, the chip air pipe 42 and the lighting electric wire 43 be set to smaller than or equal to the thickness Tc of the coils 31 to 33. In that case, the water injection pipe 41, the chip air pipe 42 and the lighting electric wire 43 do not protrude to the outside of the coils 31 to 33, and therefore, it is not necessary to form a groove as an undercut for the pipe 41 and the like on the inner circumference portion of the stator core 301 (FIG. 3) that faces the outer circumference portion of the coil unit 30.

In addition to the above holes 41H, 42H, 43H, a plurality of holes are formed on the rear flange 38, and as shown in FIG. 3, motor terminals 44U, 44V, 44W and a cooling air pipe 45 engage with rim portions of the respective holes.

The motor terminals 44U, 44V, 44W are connected with the coils 31 to 33, respectively, and are connected with the controller 9B through the electric wires in the motor 10, the connector 92 and the hose 9C. When the three-phase alternating current generated by the controller 9B is applied to the coils 31 to 33 through the motor terminals 44U, 44V, 44W, a rotating magnetic field is generated in the stator 3. By the interaction between the rotating magnetic field and a magnetic field generated by the magnet 22, the rotor 2 is rotated around the shaft 21.

The cooling air pipe 45 supplies air to the coils 31 to 33 through the hole of the rear flange 38, and thereby, cools the coils 31 to 33 and the periphery. The cooling air pipe 45 is connected with the air compressor through the connector 92 and the hose 9C.

[Holding Element of Motor]

Next, as elements for storing and holding the rotor 2 and the stator 3, the holder case 4, the rear holder 5, the motor case 6 and the ring screw 7 will be each described in order.

(Holder Case)

As shown in FIG. 3 and FIG. 6, the holder case 4 is a roughly cylindrical member including a holding portion 46 that holds the front bearing 25, and an opening 47 that is positioned at a rear end side.

A cutout 48 (FIG. 3) into which a part of the housing Lh of the light source L is inserted is formed at a front end rim portion of the holder case 4.

(Rear Holder)

The rear holder 5 includes a holding portion 51 that holds the rear bearing 26, a fitting portion 52 that is fitted to the inside of the holder case 4, and a cylinder portion 53 that protrudes from the holding portion 51 rearward. The connector 92 engages with the rear end portion of the shaft 21 that is positioned at the inside of the cylinder portion 53.

Figure 2C:
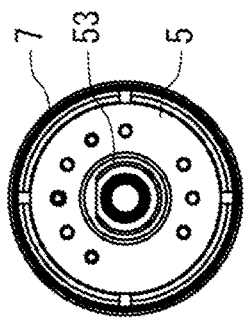
Figure 2B:
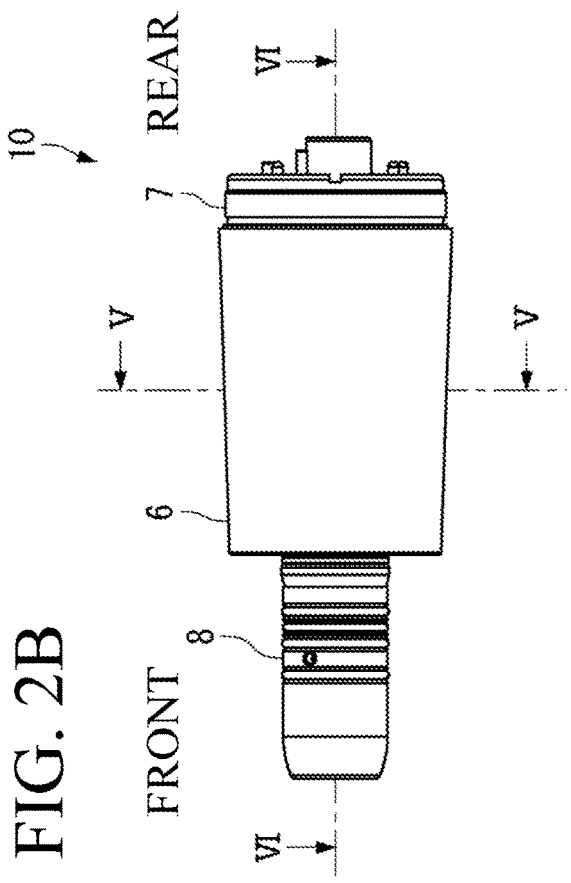
Figure 2A:
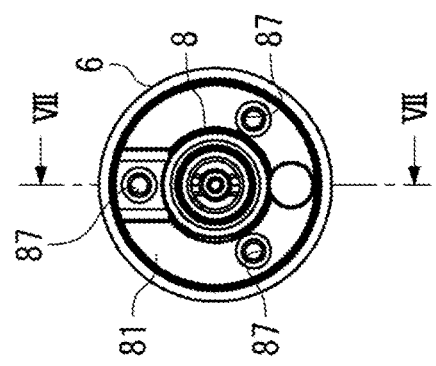

On the holding portion 51, a plurality of holes corresponding to the holes of the rear flange 38 of the bobbin 34 are formed so as to pass in the axial direction (FIG. 2C and FIG. 3).

(Motor Case)

The motor case 6 is a cylindrical member that surrounds the outer circumference portion of the holder case 4. In the motor case 6, the diameter is slightly expanded, from the front end to the rear end.

(Ring Screw)

The ring screw 7 (FIG. 3 and FIG. 6) fixes the holder case 4, the rear holder 5 and the motor case 6 at predetermined positions, respectively. A female screw that engages with screws formed on the outer circumference portion of the rear holder 5 and the outer circumference portion of the holder case 4 is formed on the inner circumference portion of the ring screw 7. A male screw that engages with a screw on the inner circumference portion of the motor case 6 is formed on the outer circumference portion of the ring screw 7. When the ring screw 7 is screwed between the holder case 4/rear holder 5 and the motor case 6, the relative positions of the constituent components of the motor 10 are determined.

[Insert Cylinder]

As shown in FIG. 3 and FIG. 6, the insert cylinder 8 includes a base portion 81 that is held in the inside of the front end of the motor case 6, and a connection portion 82 that protrudes from the base portion 81 forward. An insertion hole 83 into which the front end side of the shaft 21 is inserted is formed on the inside of the insert cylinder 8.

The connection portion 82 is inserted into the inside of a connection portion 94 of the handpiece 9A (FIG. 1), and the shaft center is matched between the shaft 21 and a shaft 93A of a rotation transmission mechanism 93 of the handpiece 9A. The shaft 21 extends to about half of the axis-directional length of the connection portion 82.

A claw clutch 86 for connecting the shaft 93A of the rotation transmission mechanism 93 and the shaft 21 is disposed at the inside of the connection portion 82. The claw clutch 86 is provided at the front end portion of the holder case 4.

The base portion 81 is formed so as to be thick enough to be surely held in the inside of the motor case 6, for supporting the connection portion 82 coaxially with the shaft 21.

On the base portion 81, a light source storage hole (FIG. 3) in which the light source L is stored is formed so as to pass through in the thickness direction.

The light source storage hole 84 is a nearly circular opening along the axial direction, and appears as a slit on the outer lateral surface of the base portion 81. The housing Lh of the light source L is fitted to the inside of the light source storage hole 84, and thereby, the position of the light source L is determined. A part of the outer lateral surface of the housing Lh of the light source L faces the inner circumference portion of the motor case 6, across the light source storage hole 84 and the cutout 48 (FIG. 3) of the holder case 4 (FIG. 5).

An inlet port of a pathway 41Z that is connected with the front end of the water injection pipe 41, an inlet port of a pathway 42Z that is connected with the front end of the chip air pipe 42, the hole 43H through which the optical fiber connected with the light source L passes, and three engagement holes 87 (FIG. 2A) are formed around the insertion hole 83 of the base portion 81.

Figure 8:
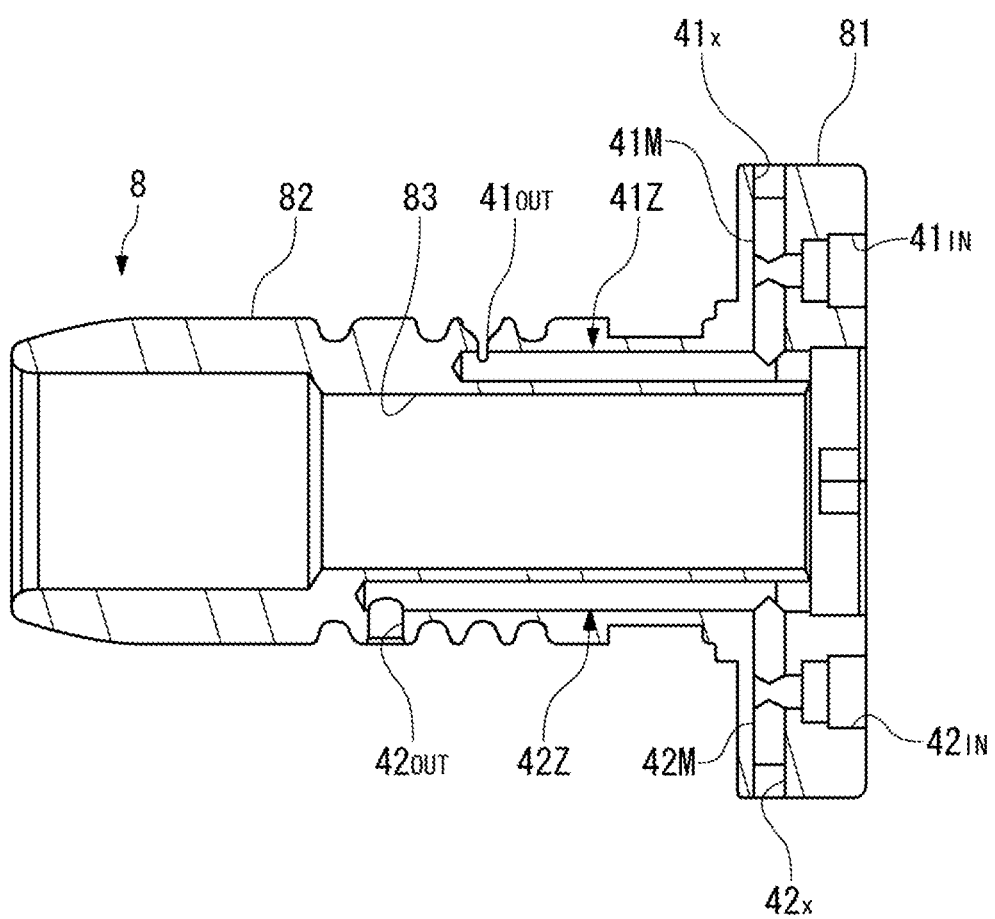
FIG. 8 is a longitudinal cross-sectional view of an insert cylinder.

FIG. 8 shows a longitudinal cross-section of the pathway 41Z and the pathway 42Z. The pathway 41Z extends from an inlet port $41_{IN}$ thereof through the interior of the base portion 81 along the insertion hole 83, in the range of the wall thickness of the connection portion 82, and leads to an outlet port $41_{OUT}$ that is positioned on the outer lateral surface of the connection portion 82. The pathway 42Z also goes on the same route from an inlet port $42_{IN}$ thereof, and leads to an outlet port $42_{OUT}$ that is positioned on the outer lateral surface of the connection portion 82.

The outlet port $41_{OUT}$ is connected with an unillustrated water injection pathway that is formed in the handpiece 9A. The outlet port $42_{OUT}$ is connected with an unillustrated chip air pathway that is formed in the handpiece 9A.

Here, in the pathway 41Z, a process hole $41_x$ for boring a section 41M that extends from the radially outer side of the base portion 81 to the radially inner side is closed afterward.

Also, a process hole $42_x$ for boring a similar section 42M in the pathway 42Z is closed afterward.

When the handpiece 9A is attached to the connection portion 82, protrusions on the handpiece 9A side engage with the engagement holes 87 (FIG. 2A), and thereby, the positions of the handpiece 9A and motor 10 in the circumferential direction are determined. Thereby, it is possible to surely connect the pipes 41, 42 and the light source L, to the pathways and optical fiber incorporated in the handpiece 9A.

Function Effect of the Embodiment

The embodiment has a structure in which the coils 31 to 33 are formed as the non-lap winding, and is characterized mainly in that each of the three medium pathways 40 that are the spaces occupied by the water injection pipe 41, the chip air pipe 42 and the lighting electric wire 43 respectively is disposed between the adjacent coils 31 to 33 at the inside of the stator core 301.

Here, the medium pathway 40 is a collective term of the spaces occupied by the water injection pipe 41, the chip air pipe 42 and the lighting electric wire 43 respectively.

The "spaces occupied" by the pipes 41, 42 and the electric wire 43 include necessary clearances at the peripheries of the pipes 41, 42 and the electric wire 43 in the adjacent-coil intervals among the coils 31 to 33 for disposing the pipes 41, 42 and the electric wire 43.

(Function Effect Compared to Lap Winding)

As the form of coils, there is also a lap winding in which coils are formed in a complex three-dimensional shape such that coil ends lap. However, in the case of the lap winding, the coil ends are ineffective magnetic regions because the lapped coil ends are thicker than coil sides.

In contrast, in the embodiment employing the non-lap winding, the stator core 301 and the rotor 2 can be provided so as to have sufficient lengths from the coil side Cs to the coil end Ce, and therefore, it is possible to enhance the performance of the motor.

Furthermore, since the coils 31 to 33 in the embodiment are formed as the non-lap winding and each has an independent and simple shape, each can be easily produced with a high quality by α winding machine.

If the medium pathways 40 are embedded in the lap winding coil, the pipes and electric wire relevant to the medium pathways 40 are buried in the coil ends, and therefore, an excessive stress is likely to be given on the coil. On the other hand, in the embodiment, the pipes 41, 42 and the electric wire 43 are disposed in the gaps set among the coils 31 to 33 that can be accurately shaped separately from the pipes 41, 42 and the electric wire 43, and thereby, the medium pathways 40 are embedded in the coil unit 30. Thereby, the medium pathways 40 can be embedded in the coil unit 30 without giving an excessive stress on the coils 31 to 33, and therefore, it is possible to secure the quality and reliability of the coils 31 to 33.

Function Effect Compared to Conventional Example of Non-Lap Winding

Even in the case of employing the non-lap winding for the coils 31 to 33, in a conventional example (FIG. 9B) of the non-lap winding, an ineffective magnetic region is generated due to the installation of the medium pathways 40.

Hereinafter, the function effect of the embodiment will be described by comparing the main characteristic (FIG. 9A) of the embodiment to the conventional example (FIG. 9B) of the non-lap winding.

As long as the medium pathways 40 are incorporated in the motor 10, a part of the region in the motor case 6 needs to be allocated for the medium pathways 40.

Figure 9A:
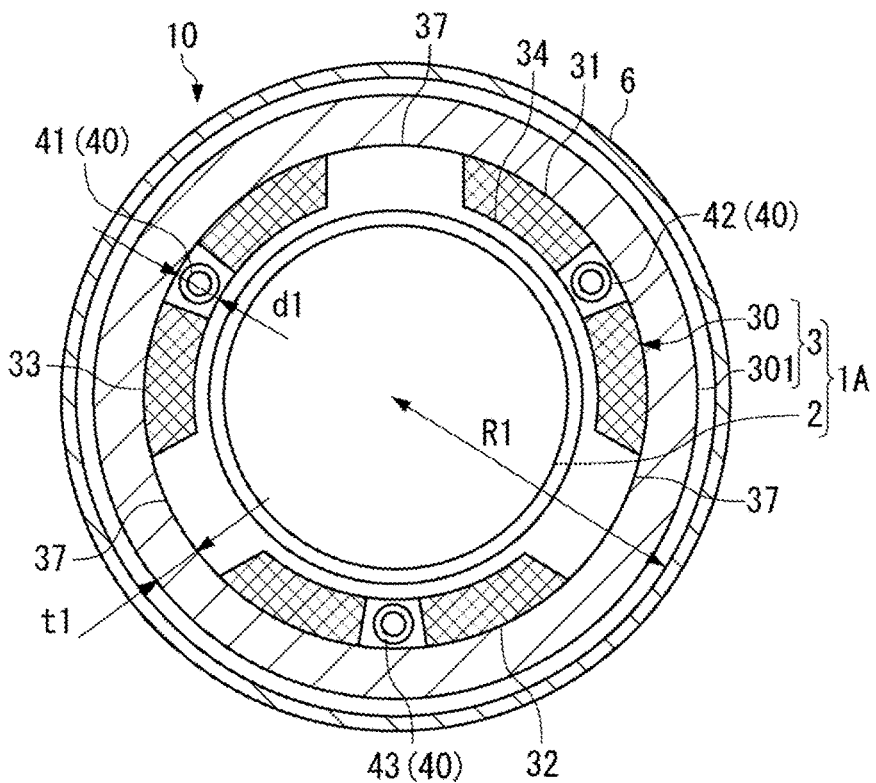
FIG. 9A is a transverse cross-sectional view schematically showing coils, a stator core and medium pathways.
Figure 9B:
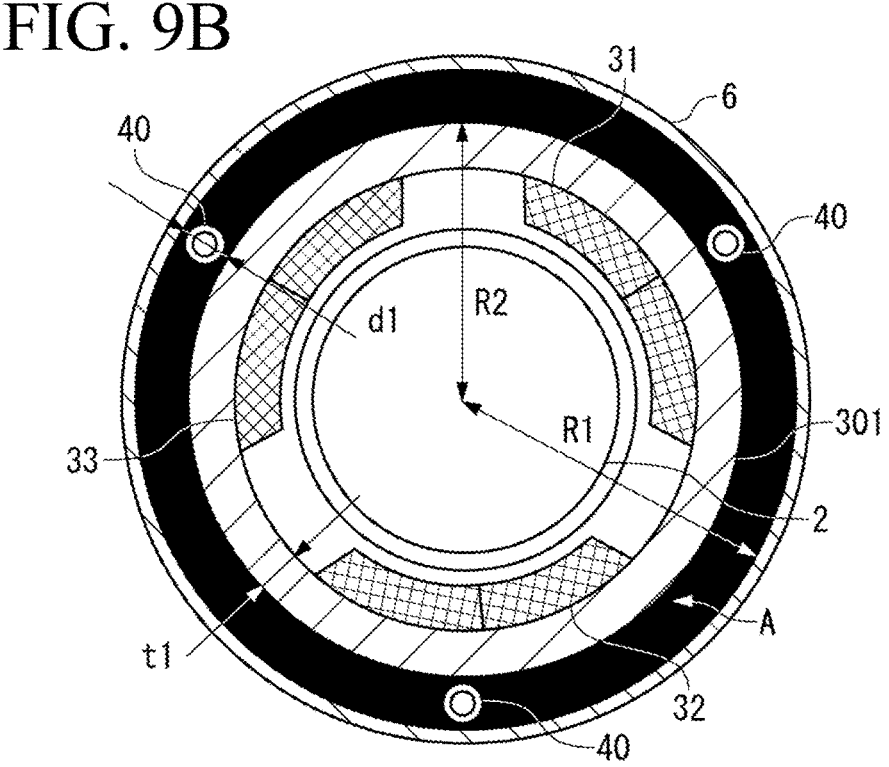
FIG. 9B is a diagram showing a conventional example and is a transverse cross-sectional view schematically showing coils, a stator core and medium pathways.

In the case where the space for disposing the medium pathways 40 is found between the stator core 301 and the motor case 6 similarly to the conventional example shown in FIG. 9B, it is necessary to provide a gap having a size corresponding to the thicknesses (outer diameters) of the pipes 41, 42 and electric wire 43 relevant to the medium pathways 40, between the outer circumference portion of the stator core 301 and the inner circumference portion of the motor case 6. A region A between the outer circumference portion of the stator core 301 and the inner circumference portion of the motor case 6 is a space that is necessary only for disposing the medium pathways 40. The region A is positioned at the outside of the main element 1A (the rotor 2 and the stator 3) that performs the drive of the motor 10, and is an ineffective region that does not contribute to the magnetic circuit at all. Among the medium pathways 40, members for performing the positioning of the medium pathways 40 are disposed.

In FIG. 9B, the whole of the region A in the motor case 6 is necessary for the medium pathways 40. The region A is positioned at the radially outermost side in the internal space of the motor case 6, and extends over the whole circumference. Therefore, the ratio to the opening area in the motor case 6 becomes a non-negligible value, for example, as much as 5 to 20%. The effective space in the motor case 6 that can be magnetically utilized is decreased by a volume in which the region A continues by the axial length of the motor in the direction orthogonal to the sheet plane of FIG. 9B.

Therefore, when the diameter of the motor case 6 is reduced for downsizing, it is not possible to secure the outer diameter of the main element 1A of the motor that is necessary for bringing out a predetermined motor output, resulting in a significant decrease in performance. For bringing out the motor output, it is necessary to increase the winding number of the coils 31 to 33, or increase the cross-section areas of the rotor 2 and the stator core 301, and therefore, it is important to secure the outer diameter of the main element 1A of the motor.

In FIG. 9B, when a large outer diameter is secured as the outer diameter of the main element 1A for achieving the performance enhancement, the diameter of the motor is remarkably increased because the medium pathways 40 is provided at the outer circumference side of the main element 1A (at the outside of the stator core 301).

Meanwhile, in the embodiment shown in FIG. 9A, each medium pathway 40 is disposed between the adjacent coils 31 to 33. Therefore, the space for disposing the medium pathways 40 is not necessary, at the outside of the stator core 301. In the embodiment, the pipes 41, 42 and electric wire 43 relevant to the medium pathways 40 are integrated with the coil unit 30, and the medium pathways 40 are embedded in the interior of the main element 1A. Specifically, at the position of the coils 31 to 33, the water injection pipe 41, the coil 31, the chip air pipe 42, the coil 32, the lighting electric wire 43 and the coil 33 are disposed in order, in the circumferential direction.

An ineffective region that appears other than the region for the medium pathways 40 when the medium pathways 40 are incorporated in the motor 10 will be discussed.

In the conventional example, the ineffective region is a region that extends in the circumferential direction among the medium pathways 40 (the region colored in black in FIG. 9B). The ineffective region spreads over a wide range, in the region A between the stator core 301 and the motor case 6.

Here, when the radius of the outer diameter of the stator core 301 is R2, the radius of the inner diameter of the motor case 6 is R1, each of the diameters of the medium pathways 40 is d1, and the number of the medium pathways 40 is n (3 in the embodiment), the area of the ineffective region is $\pi(R1^2-R2^2-n(d1/2)^2)$.

On the other hand, in the embodiment (FIG. 9A), the stator core 301 can be disposed so as to be extremely close to the inner circumferential surface of the motor case 6, and the ineffective region is not substantially generated.

Here, in both of the FIG. 9B and FIG. 9A, an equivalent clearance is provided between the inner circumferential surface of the motor case 6 and the member facing this (the pipes 41, 42 and electric wire 43 relevant to the medium pathways 40 in FIG. 9B, or the stator core 301 in FIG. 9A), and therefore, it is not necessary to consider the clearance, in the comparative discussion of the space efficiencies of the two.

Since such an ineffective region is not generated, the embodiment has an advantage over the conventional example, when the outer diameter of the main element 1A is increased. It is possible to enhance the performance of the motor 10, by increasing the outer diameter of the main element 1A, that is, by increasing the winding number of the coils 31 to 33 or increasing the cross-section areas of the rotor 2 and the stator core 301.

This will be described, taking as an example the increase in the cross-section area of the stator core 301.

The radius of the outer diameter of the stator core 301 in FIG. 9B is put as R2. Further, in each of FIGS. 9B and 9A, the radius of the inner diameter of the motor case 6 is put as R1, the diameter of the medium pathway 40 is put as d1, and the wall thickness of the stator core 301 is put as t1. It is assumed that R1=R2+d1 holds.

First, in the conventional example shown in FIG. 9B, the cross-section area A2 of the stator core 301 is shown by the following Formula (1).

$$A2=\pi(R2^2-(R2-t1)^2) \tag{1}$$

Next, in the embodiment shown in FIG. 9A, the cross-section A1 of the stator core 301 is shown by the following Formula (2).

$$A1=\pi(R1^2-(R1-t1)^2) \tag{2}$$

By the calculation of the difference ΔA in the cross-section of the stator core 301 between the embodiment and the conventional example, that is, (A1-A2), the following Formula (3) is obtained.

$$\Delta A=2\pi t1 d1 \tag{3}$$

Using Formula (3), specific examples of numerical values are shown.

In the case of t1=2 mm and d1=2 mm, ΔA is $8\pi$ mm$^2$, by turning them into Formula (3).

Then, in the case of R2=10 mm, A2=$36\pi$ mm$^2$ holds, and ΔA is added to this so that A1 is $44\pi$ mm$^2$.

Accordingly, the cross-section area of the stator core 301 can be increased about 1.22 times, by A1/A2. By that quantity, it is possible to enhance the performance of the motor 10.

Thus, according to the embodiment, it is possible to use the whole space in the motor case 6, only by the elements that contribute to the performance, as much as possible.

Therefore, even when the diameter of the motor case 6 is reduced for downsizing, it is possible to secure the outer diameter of the main element 1A of the motor 10 that is appropriate to a required high output.

Alternatively, it is possible to maintain a small diameter of the motor case 6, while securing a large outer diameter as the outer diameter of the main element 1A for achieving the performance enhancement. That is, according to the embodiment, it is possible to achieve a small high-performance motor 10.

Further, according to the embodiment in which the medium pathway 40 is disposed between the adjacent coils 31 to 33, it is only necessary to form, on the bobbin 34, the flanges 38, 39 that the medium pathway 40 penetrates, for incorporating the medium pathway 40 into the coil unit 30. That is, it is possible to easily incorporate the medium pathway 40 into the coil unit 30, by the slight change in the shape of the bobbin 34 that does not exert influence on the characteristic of the motor, without adding a new member other than the bobbin 34 that supports the coils 31 to 33.

In addition to the above description, according to the embodiment, foreign substances are unlikely to accumulate in the water injection pipe 41 and the chip air pipe 42, compared to the conventional example of the non-lap winding, and therefore, it is possible to stably supply water and air.

In the conventional example (FIG. 9B), the medium pathways 40 are positioned at the radially outermost side in the internal space of the motor case 6. However, the tubes 951, 952 (FIG. 1) on the hose 9C side that are connected with the rear ends of the medium pathways 40 do not pass through positions that are greatly distant from the shaft center. When there is a large positional difference between the medium pathways 40 and the tubes 951, 952 on the hose 9C side in this way, the medium pathways 40 are located toward the tubes while the interference with peripheral structures is avoided. As a result, bending portions are generated on the pathways, and foreign substances are likely to accumulate at the bending portions.

In the embodiment, the medium pathways 40 are not disposed at the outside of the stator core 301, and are disposed at the inside of the stator core 301. Therefore, the distance from the shaft center is equivalent between the medium pathways 40 and the tubes 951, 952 on the hose 9C side.

Therefore, through a simple route, the medium pathways 40 can be connected with the tubes 951, 952 prepared in the hose 9C. Accordingly, bending portions having small curvature radiuses are not generated, and the medium pathways 40 can be smoothly connected to the tubes, allowing for the avoidance of the accumulation of foreign substances.

In particular, when the corresponding medium pathway 40 is disposed on an extended line of each of the tubes 951, 952 prepared in the hose 9C, it is possible to avoid the accumulation of foreign substances more surely.

(Installation of Light Source)

Next, a structure for installing the light source L connected with the lighting electric wire 43 will be described.

First, the housing Lh of the light source L is engaged with the protrusion 391 (FIG. 7) that protrudes forward from the front flange 39 of the bobbin 34, and thereby, the light source L is incorporated into the front side of the front flange 39. Thereby, it is possible to achieve the diameter reduction of the motor 10, compared to the case where the installation space for the light source L is prepared at the outside of the holder case 4, for example.

Further, the light source L is stored in the light source storage hole 84 of the base portion 81 of the insert cylinder 8. Thereby, it is possible to perform the downsizing of the motor 10 in the axial direction.

Then, the space necessary for the installation of the light source L has no room with respect to the radius of the motor case 6. Therefore, the light source storage hole 84 is opened also on the outer lateral surface of the base portion 81 (FIG. 3), and the cutout 48 (FIG. 3) is formed on the outer circumference portion of the front end of the holder case 4 on which the base portion 81 abuts. Thereby, it is possible to dispose the inner circumference portion of the motor case 6 at the close vicinity of the outer lateral surface of the housing Lh of the light source L that is exposed across the light source storage hole 84 and the cutout 48 (FIG. 5), and to perform a further diameter reduction of the motor case 6.

[Improvement of Coil]

In the embodiment employing the non-lap winding, unlike the lap winding, it is possible to use the coils 31 to 33 that are shaped individually, and therefore, it is possible to surely increase the space factor of the coils 31 to 33, by applying a predetermined winding way to each of the coils 31 to 33. The space factor is the proportion of the cross-section area of conductors to the cross-section area of the coil.

Examples of the winding way allowing the space factor to increase include an aligned winding in which a copper wire is regularly aligned, an α winding in which both of the starting end and trailing end of the winding wire are positioned at the outside of the coil, and a bundle wire winding in which a bundle wire resulting from bundling thin element wires is used. Further, in the case of using a rectangular wire having a rectangular cross-section, the wire can be wound more densely than in the case of a round wire, resulting in the enhancement of the space factor. From a standpoint of the enhancement of the space factor, the α winding with a flat wire is most suitable.

Further, for reducing the eddy-current loss that is generated in the coils 31 to 33, it is preferable to configure the coils 31 to 33 by a bundle wire resulting from bundling thin element wires. In particular, this is effective in the case where it is necessary to increase the cross-section area of the conductive wire for reducing the coil resistance.

This will be described with reference to FIGS. 10A to 10C.

Figure 10A:
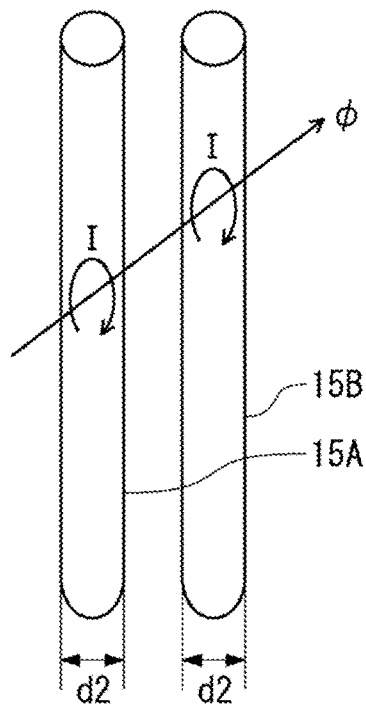
FIG. 10A to FIG. 10C are diagrams for describing a modification of the coil in the present invention.

FIG. 10A schematically shows a manner in which a plurality of thin element wires 15A, 15B are bundled. Here, the bundle wire may be configured to include another unillustrated element wire.

When a magnetic flux $\phi$ is interlinked with the element wires 15A, 15B, an eddy current I flows through each of the element wires 15A, 15B so as to interfere with the change in the magnetic flux $\phi$. An eddy-current loss Pe to be generated by the eddy current I is expressed by the following formula.

$$Pe = Ke(tfBm)^2/\rho$$

t: plate thickness
f: frequency
Bm: maximum magnetic flux density
$\rho$: resistivity of magnetic substance
Ke: proportional constant As for the eddy-current loss Pe, when the variables other than the plate thickness t are fixed values, $Pe \propto t^2$ holds. On this occasion, when the number of cores is N and the total thickness is D, $t = D/N$ holds.

Therefore, $Pe \propto N \times t^2 = N \times (D/N)^2 = D^2/N$ holds.

That is, by increasing N, it is possible to reduce the eddy-current loss Pe.

For the coil, this can be considered by using t to resemble the diameter of the element wire and using N to resemble the number of the element wires.

For the coil, Pe can be reduced by decreasing the diameter of the element wire and increasing the number of the element wires as much as possible.

Figure 10B:
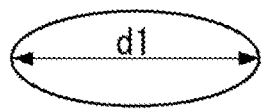
Figure 10C:
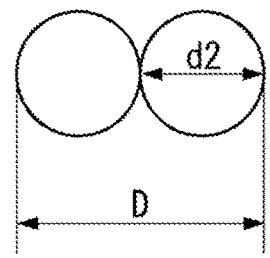
Figure 11A:
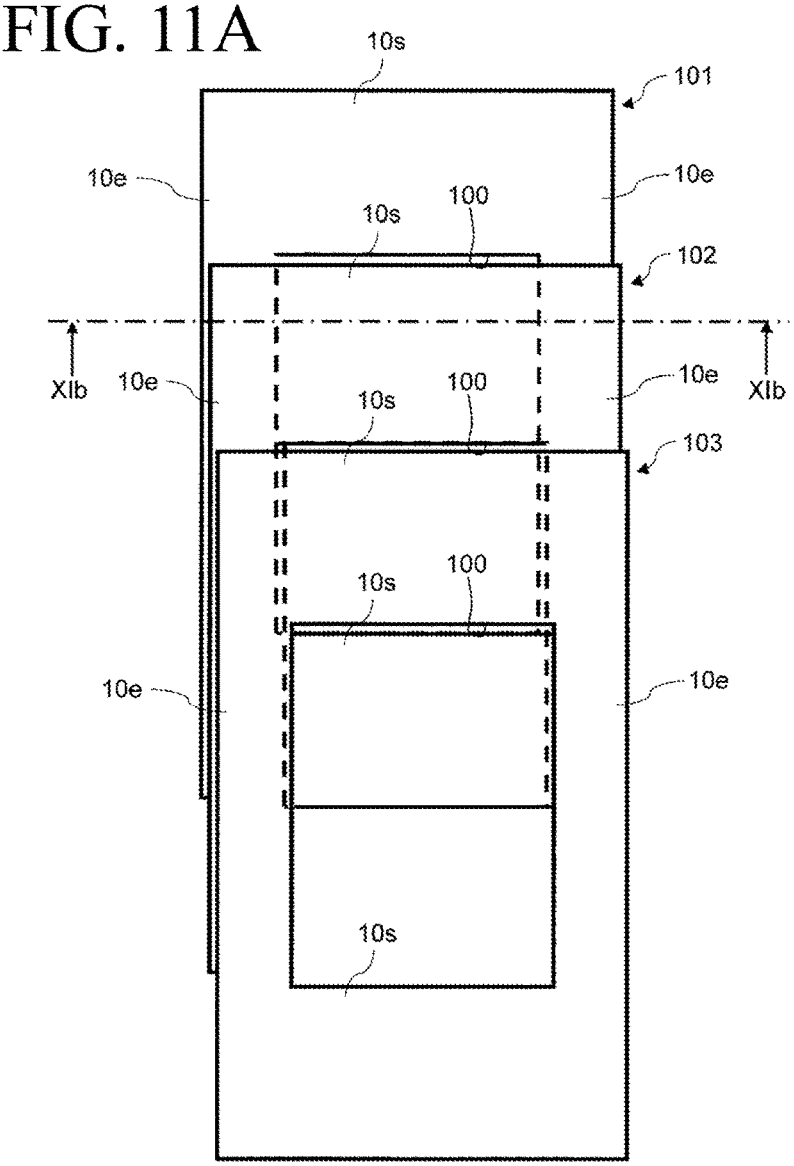
FIG. 11A is a development view of coils.
Figure 11B:
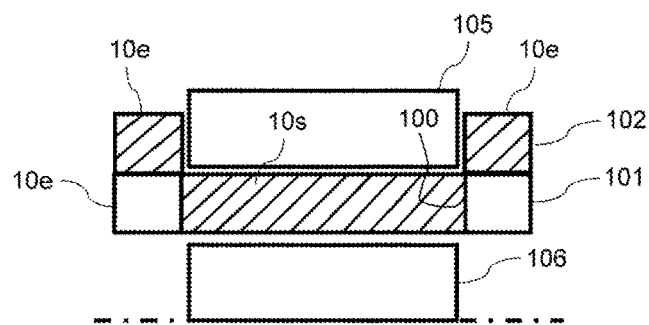
FIG. 11B is a XIb-XIb line schematic cross-sectional view of a rotor, coils and a stator core in FIG. 11A.

For example, for convenience sake, the long diameter d1 of an oval in FIG. 10B is two-divided into diameters d2 in FIG. 10C. On this occasion, the total thickness D can be regarded as d1, and N can be regarded as 2. Therefore, the thin bundle wire in FIG. 10C can reduce Pe to ½, relative to the thick wire in FIG. 10B. Thereby, the heat generation due to the eddy-current loss is sufficiently suppressed, allowing for the contribution to the enhancement of the motor performance.

The electric motor in the present invention can be appropriately configured, regardless of the scheme and kind of the drive, the materials of the constituent components and the like, as long as it is a brushless slotless type and includes a medium pathway through which a medium supplied for actualizing the function of the application object of the electric motor passes.

In the above embodiment, the coils 31 to 33 are held in the bobbin 34, but may be held in the inner circumference portion of the stator core 301.

Further, the electric motor in the present invention only needs to include at least one medium pathway. That is, the medium pathway does not need to be disposed in all gaps respectively existing in the adjacent-coil intervals among the plurality of coils, and the medium pathway 40 only needs to be disposed in at least one gap.

The electric motor in the present invention can be suitably applied to a handpiece that is used for dental treatment and technique.

Further, the electric motor in the present invention is not limited to dentistry, and can be applied to medical handpieces that are used in all medical fields.

Furthermore, the electric motor in the present invention can be used while being embedded in a machine tool. For example, the electric motor in the present invention can be configured to drive a spindle of a machine tool and to include medium pathways through which media such as water and air supplied to a work for various purposes pass.

In addition, the electric motor in the present invention can be used for various usages.

Other than the above descriptions, without departing from the spirit of the present invention, it is allowed to make a choice from the configurations described in the above embodiment, or appropriately change into another configuration.

REFERENCE SIGNS LIST 1A main element
2 rotor
3 stator
4 holder case
5 rear holder
6 motor case
7 ring screw
8 insert cylinder
9A handpiece
9B controller
9C hose
10 motor
15A, 15B element wire
21 shaft
22 magnet
22A segment
23 cover holder
25 front bearing
26 rear bearing
27 central portion
28 front end portion
29 rear end portion
30 coil unit
31 to 33 coil
34 bobbin (holder member)
35 opening
36 cylinder portion
37 convex portion
38 rear flange
39 front flange
40 medium pathway
41 water injection pipe (medium pathway, first pipe)
41H hole
42 chip air pipe (medium pathway, second pipe)
42H hole
43 lighting electric wire (medium pathway)
43H hole
44U, 44V, 44W motor terminal
45 cooling air pipe
46 holding portion
47 opening
48 cutout
51 holding portion
52 fitting portion
53 cylinder portion
81 base portion
82 connection portion
83 insertion hole
84 light source storage hole
86 claw clutch
87 engagement hole
91 tool
92 connector
93 rotation transmission mechanism
94 connection portion
231 cover portion
232 front end portion
301 stator core
391 protrusion
401 metal pipe
402 resin cover
403 engagement portion
430 wiring portion
431, 432 lighting terminal
951, 952 tube
A region
d1, d2 diameter
I eddy current
L light source
Ld light emitting device
Lh housing
Sp gap

The invention claimed is:

1. A brushless electric motor comprising:
a stator that includes a stator core and a plurality of coils, the plurality of coils being disposed at an inner circumference side of the stator core;
a rotor that includes a shaft, the rotor being rotated around the shaft with respect to the stator;

a medium pathway through which a medium passes, the medium being used for actualizing a function of an application object of the electric motor; and a holder member that holds the plurality of coils, wherein the plurality of coils are adjacent to each other in a rotation direction of the rotor so as not to lap mutually, wherein the medium pathway is disposed between the adjacent coils, wherein the holder member includes:
- a cylinder portion, the plurality of coils being disposed on an outer circumference of the cylinder portion, and
- a flange that is formed integrally as a single unit with the cylinder portion to project from the cylinder portion in a radially outward direction, and
- a plurality of convex portions that are arranged to protrude from the outer circumference of the cylinder portion, wherein each of the plurality of coils is configured to be fitted to one of the plurality of convex portions, and wherein the medium pathway penetrates the flange.

2. The electric motor according to claim 1,
wherein the medium pathway is a space occupied by a pipe through which a fluid as the medium passes, and
a thickness of the pipe is set to smaller than or equal to a thickness of the coil.

3. The electric motor according to claim 1,
wherein the medium pathway is a space occupied by an electric wire as the medium, and
a thickness of the electric wire is set to smaller than or equal to a thickness of the coil.

4. The electric motor according to claim 1,
wherein the stator includes three coils as the coil, and the rotor includes four poles.

5. The electric motor according to claim 1,
wherein the electric motor drives a dental handpiece that is the application object, and
includes, as the medium pathway, a pathway through which water to be supplied into the dental handpiece passes, and a pathway through which air to be supplied into the dental handpiece passes.

6. The electric motor according to claim 2,
wherein the electric motor drives a dental handpiece that is the application object, and
includes, as the pipe, a first pipe through which water to be supplied into the dental handpiece passes, and a second pipe through which air to be supplied into the dental handpiece passes.

7. A dental device comprising:
the electric motor according to claim 1;
a dental handpiece that is driven by the electric motor; and
a controller that performs drive control of the electric motor.

8. A dental device comprising:
the electric motor according to claim 2;
a dental handpiece that is driven by the electric motor; and
a controller that performs drive control of the electric motor.

9. The dental device according to claim 7,
wherein the electric motor is connected with the controller through a hose, and
the medium pathway is positioned on an extended line or approximately on an extended line of a pathway that is formed in the hose.

10. The dental device according to claim 8,
wherein the electric motor is connected with the controller through a hose, and
the medium pathway is positioned on an extended line or approximately on an extended line of a pathway that is formed in the hose.

11. The electric motor according to claim 1,
wherein the flange is formed at one end or both ends of the holder member.

12. The electric motor according to claim 1,
wherein the flange comprises a rim portion and a plurality of holes formed in the rim portion.

13. The electric motor according to claim 1,
wherein each of the plurality of convex portions is configured to be received in a complementary opening of each of the plurality of coils to position and hold each of the plurality of coils in the circumferential direction of the cylinder portion.

14. The electric motor according to claim 1,
wherein the plurality of convex portions are arranged at regular intervals in the circumferential direction of the cylinder portion.

15. The electric motor according to claim 1,
wherein each of the plurality of convex portions has a height nearly equal to a thickness of the coil, said height being measured along a radial direction of the cylinder portion.

16. The electric motor according to claim 1,
wherein the flange projects from the cylinder portion by a size equivalent to a height of each of the plurality of convex portions, said height being measured along a radial direction of the cylinder portion.

* * * * *